United States Patent [19]
Agback et al.

[11] Patent Number: 4,725,676
[45] Date of Patent: Feb. 16, 1988

[54] 5-(3,5-DISUBSTITUTED PHENYLAZO)-2-HYDROXYBENZENE-ACETIC ACIDS AND SALTS AND LACTONES THEREOF HAVING A POTENTIALLY INHIBITORY EFFECT ON 15-HYDROXY-PROSTAGLANDIN DEHYDROGENASE

[75] Inventors: Karl H. Agback, Upsala; Alf S. Nygren, Örbyhus, both of Sweden

[73] Assignee: Pharmacia AB, Upsala, Sweden

[21] Appl. No.: 882,896

[22] PCT Filed: Nov. 13, 1985

[86] PCT No.: PCT/SE85/00453

§ 371 Date: Jul. 3, 1986

§ 102(e) Date: Jul. 3, 1986

[87] PCT Pub. No.: WO86/03195

PCT Pub. Date: Jun. 5, 1986

[30] Foreign Application Priority Data

Nov. 23, 1984 [SE] Sweden .................. 8405924

[51] Int. Cl.[4] .................. A61K 31/655; C07C 107/06; C07D 307/83
[52] U.S. Cl. .................. 534/853; 534/728; 534/787
[58] Field of Search .................. 260/851, 853, 660; 514/155, 156; 534/728, 787

[56] References Cited

U.S. PATENT DOCUMENTS

| 3,236,829 | 2/1966 | May et al. | 534/851 X |
| 3,244,694 | 4/1966 | May et al. | 534/851 X |
| 3,251,822 | 5/1966 | May et al. | 534/851 X |
| 4,412,992 | 11/1983 | Chan | 534/851 |

FOREIGN PATENT DOCUMENTS

| 0036637 | 9/1981 | European Pat. Off. | 534/660 |
| 0021229 | 12/1982 | European Pat. Off. | 534/851 |
| 0045006 | 12/1982 | European Pat. Off. | 534/660 |
| 0066861 | 12/1982 | European Pat. Off. | 534/660 |
| 3408152 | 9/1985 | Fed. Rep. of Germany | 534/851 |
| 2093833 | 9/1982 | United Kingdom | 534/660 |

OTHER PUBLICATIONS

Berry et al, Biochemical Pharmacol., vol. 32, pp. 2863 to 2871 (1983).

Moore et al, Biochemical Pharmacol., vol. 31, pp. 969 to 971 (1982).

Primary Examiner—Floyd D. Higel
Attorney, Agent, or Firm—Fred Philpitt

[57] ABSTRACT

The present invention is concerned with azo compounds having the structure

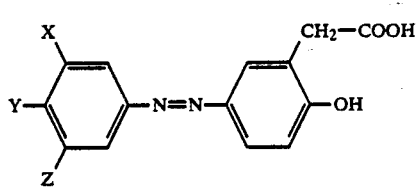

in which:
Y is hydrogen, and
X and Z are carboxy or lower alkoxycarbonyl, or the lactones or salts of said azo compound, such compounds being useful in pharmaceutical compositions and being specifically useful to inhibit 15-prostaglandin dehydrogenase (PGDH).

5 Claims, No Drawings

5-(3,5-DISUBSTITUTED PHENYLAZO)-2-HYDROXYBENZENE-ACETIC ACIDS AND SALTS AND LACTONES THEREOF HAVING A POTENTIALLY INHIBITORY EFFECT ON 15-HYDROXY-PROSTAGLANDIN DEHYDROGENASE

The present invention is concerned with novel compounds having a potentially inhibitory effect on 15-hydroxyprostaglandin dehydrogenase (PGDH). The invention is also concerned with the production of these novel compounds and with pharmaceutical compositions containing them.

The future potentialities of PGDH inhibitors, in respect of their usefulness in medicine, have not yet been fully explored. But it is a known fact that prostaglandins play a very important role in the body's regulating system, and for this reason any drugs interfering with either the synthesis or the degradation of prostaglandins may be potentially valuable medical tools. The so-called cytoprotective effect of prostaglandins is relatively well known in the context of ulcer therapies; but neverthless prostaglandin administration has not been utilized to any major extent for therapeutic purposes because the prostaglandins administered with survive in vivo for only a very short time. A drug inhibiting the degradation of endogenous prostaglandins might conceivably be much more successful than prostaglandin administration.

Endogenous prostaglandins have a major role also in inflammatory processes. In the treatment of rheumatoid arthritis it is therefore at present quite a common practice to employ inhibitors of prostaglandin synthesis; but nowadays this is regarded as merely being a symptomatic treatment, and as a matter of fact some of the prostaglandins are now believed to possibly have a very favorble effect. Thus in this context, too, the inhibition of PGDH dependent degradation may be potentially very valuable. Further potentially valuable medical fields of application for the present novel compounds are all those where prostaglandins may function as desirable controlling factors as e.g. in the case of circulatory disorders, cancer, fertility, cell regulation etc.

Examples of previously known compounds having an inhibitory effect on PGDH are such azo compounds as are set forth in No. EP-A-21229 and novel arylacetic acid derivatives set forth in Swedish patent application No. 8400239-3.

It is an object of the present invention to provide improved PGDH inhibitors and methods for their production. Further objects are to provide improved pharmaceutical compositions and treating methods involving such inhibitors.

The novel compounds of the present invention have the following structure:

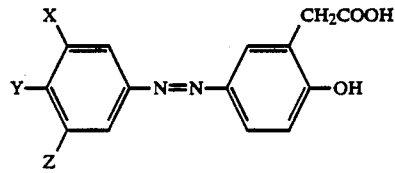

(I)

in which X, Y and Z are hydrogen, carboxy or lower alkoxycarbonyl, one of X, Y and Z always being hydrogen and the others being identical or different groups.

The invention comprises also lactones of compounds (I) and salts thereof. The preferred salts are pharmaceutically acceptable and therapeutically active.

By lower alkoxy groups are meant those having less than seven carbon atoms.

Suitable salts are metal salts such as the sodium, potassium and calcium salts, or salts with organic amines such as e.g. diethanolamine, triethanolamine, N-methylglucamine, trishydroxymethyl-methylamine etc.

A major advantage of the compounds according to the present invention resides in that they comprise groups greatly varying inter se in respect to their capacity of being absorbed from the gastrointestinal tract. This means that the invention comprises i.a. compounds which are rapidly and completely absorbed into the bloodstream—which is a valuable feature for obtaining a systemic effect. Other compound, on the other hand, have a very low capacity for being absorbed and consequently will concentrate to the gastrointestinal tract; so this in turn means that some compounds of formula (I) may have a potential local activity against gastrointestinal disorders such as for instance gastric ulcer, Crohn's disease and ulcerous colitis.

It has been found, surprisingly, that the novel compounds are extremely potent inhibitors of the enzyme PGDH. Moreover an important feature of these compounds is that they are highly selective in their effect: Their inhibition of cyclooxygenase is practically zero. The invention permits treatments with very low doses of the active substance, which in turn means that particular ways of administration may be resorted to that would otherwise be entirely out of the question—e.g. inhalation of the substance in the form of an aerosol. The extremely high potency of the novel compounds moreover minimizes the risk of toxic side effects due to metabolites, especially metabolites of the aromatic amine type formed by splitting of the azo bridge.

The compounds of formula (I) are produced in a manner known per se by diazotation of amines of the general formula

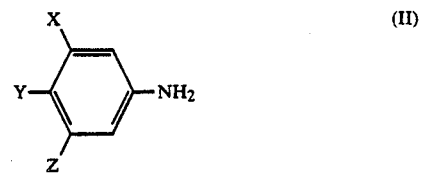

(II)

in which X, Y and Z have the same meanings as above, and coupling with 2-hydroxybenzeneacetic acid in an alkaline medium, followed by rapid neutralization and isolation of the product.

A compound of formula (I) may be converted to the corresponding lactone of the general formula

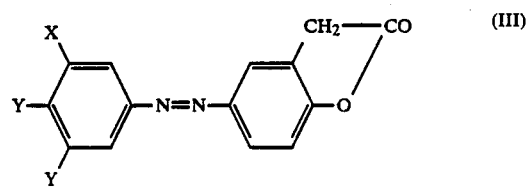

(III)

or a lactone of formula (III) may be converted to a compound of formula (I).

Conversion to the lactone may be performed in a simple manner by reaction with acids, if desired in the presence of water-withdrawing agents such as e.g. acetic anhydride or thionyl chloride, or under other conditions that will remove water such as e.g. azeotropic distillation of water.

The lactones according to the invention can readily be converted to corresponding acids by gentle alkaline hydrolysis and subsequent acidification.

A compound of this invention containing at least one free carboxy group B readily convertible to corresponding salts by reaction with an equivalent amount of a suitable salt-forming reagent such as for example sodium hydroxide, potassium hydroxide or a suitable organic amine, at a pH suitable for the compound contemplated and in the presence of a solvent. The salt may be prepared either in a solid state by means of solvent removal in a known per se manner, or if solubility permits directly in solution, preferably aqueous solution, for direct pharmaceutical use.

The novel pharmaceutical compositions of this invention contain a therapeutically active amount of a compound of formula (I) or a lactone thereof or a salt of those compounds that contain at least one carboxy group, if desired in combination with an inert, organic or inorganic carrier material which is suitable for oral, rectal, buccal or parenteral administration or for inhalation. The pharmaceutical compositions may be prepared in solid form or may be semisolid or liquid; optionally they may be sterilized and/or contain additional adjuvants. They may be produced in a manner well known to persons skilled in the art, the active substance being mixed with the carrier material and with further adjuvants (if any), and the resultant mixture being converted to a suitable galenic form. As a general guideline for suitable dosages may be mentioned doses of 0.01–100 mg/day for a person weighing 75 kg.

According to the novel treating method of this invention for the inhibition of PGDH, a pharmaceutical composition containing a therapeutically active amount of a compound of formula (I) or a lactone thereof or a salt of those compounds that contain at least one carboxy group is administered to a mammal, including man.

The compound of this invention may be for instance 5-(3,5-dicarboxy-phenylazo)-2-hydroxy-benzeneacetic acid, its lactone and salts thereof the corresponding 3-monomethyl ester, its lactone and salts thereof the corresponding 3,5-dimethyl ester, its lactone and salts thereof the corresponding 3-monoethyl ester, its lactone and salts thereof the corresponding 3,5-diethyl ester, its lactone and salts thereof the corresponding 3-ethyl-5-methyl ester, its lactone and salts thereof the corresponding 3-propyl ester, its lactone and salts theeof the corresponding 3-isopropyl ester, its lactone and salts thereof the corresponding 3,5-dipropyl ester, its lactone and salts thereof the corresponding 3-butyl ester, its lactone and salts thereof the corresponding 3-isobutyl ester, its lactone and salts thereof the corresponding 3-pentyl ester, its lactone and salts thereof the corresponding 3-hexyl ester, its lactone and salts thereof 5-(3,4-dicarboxy-phenylazo)-2-hydroxy-benzeneacetic acid, its lactone and salts thereof the corresponding 3-monomethyl ester, its lactone and salts thereof the corresponding 4-monomethyl ester, its lactone and salts thereof the corresponding 3,4-dimethyl ester, its lactone and salts thereof the corresponding 3-monoethyl ester, its lactone and salts thereof the corresponding 4-monoethyl ester, its lactone and salts thereof the corresponding 3,4-diethyl ester, its lactone and salts thereof the corresponding 3-ethyl-4-methyl ester, its lactone and salts thereof the corresponding 3-methyl-4-ethyl ester, its lactone and salts thereof the corresponding 3-propyl ester, its lactone and salts thereof the corresponding 4-propyl ester, its lactone and salts thereof the corresponding 3-isopropyl ester, its lactone and salts thereof the corresponding 4-isopropyl ester, its lactone and salts thereof.

The below working examples illustrate various embodiments of the invention without limiting its scope.

EXAMPLE 1

5-(3,4-bis-(methoxycarbonyl)-phenylazo)-2-hydroxy-phenylacetic acid 24 g of dimethyl-4-nitro-benzene-1,2-dicarboxylate was dissolved in 500 ml of acetic acid, whereupon 2 g of 10% palladium on carbon, suspended in 10 ml of hydrochloric acid, was added.

The suspension was hydrogenated, filtered and evaporated. To the residue were added 2 ml of hydrochloric acid and ethyl acetate so as to precipitate crystals which were then filtered off and washed with ethyl acetate and petroleum ether.

The hydrochloride was dissolved in 100 ml of $H_2O$ and 10 ml of hydrochloric acid. The solution was cooled with 50 g of ice and diazotized with 7 g of sodium nitrite dissolved in 30 ml of water. The diazonium salt solution was added to an ice-cooled solution of 30 g of 2-hydroxyphenyl acetic acid in 24 g o sodium hydroxide and 200 ml of water. After 15 seconds the solution was acidified with hydrochloric acid and extracted with ethyl acetate. The ethyl acetate solution was shaken against water, dried, treated with active carbon and evaporated. The residue was leached with chloroform. The residue then obtained was dissolved in methanol-water (about 20%) and treated vith active carbon wile hot (about 80° C.). More hot water was added until opalescence was obtained, and the solution was again treated with active carbon. It was then cooled, and the crystals were filtered off and recrystallized from acetonitrile-ethylene dichloride. The crystals were dried for 4 hours at 100° C.

Yield 12 g. Melting point 196° C. (not stage).

NMR analysis confirmed the structure of the substance.

| Elemental analysis: | | |
|---|---|---|
| | Calculated | Found |
| C | 58.06 | 58.1 |
| H | 4.33 | 4.3 |
| N | 7.53 | 7.5 |

EXAMPLE 2

5-(3,5-bis-(methoxycarbonyl)-phenylazo)-2-hydroxy-phenylacetic acid 20.9 g of dimethyl-5-amino-benzene-1,3-dicarboxylate was dissolved in 20 ml of concentrated hydrochloric acid in 200 ml of ice water. The solution was diazotized with 7 g of sodium nitrite dissolved in 30 ml of water. 30.4 g of 2-hydroxy-phenylacetic acid was dissolved in 200 ml of water and 24 g of sodium hydroxide. The solution was cooled with 100 g of ice. To this hydroxide solution was then added the diazonium salt solution, all at once, and with vigorous stirring. After 30 seconds the solution was acidified with acetic acid and the precipitate was filtered off. The precipitate was leached with an about 25% ethanol solution which was then diluted with water until a state of weak opalescence was reached. The solution was treated with active carbon and evaporated down to half its volume. Sodium hydrogen carbonate was added until the solution was clear, whereupon the solution was heated (80° C.) and acidified with hydrochloric acid. The solution was cooled, the crystals were filtered off and dried.

Yield 24 g.
Melting point 232° C.
NMR analysis confirmed the structure of the substance.

| Elemental analysis: | | |
|---|---|---|
| | Calculated | Found |
| C | 58.06 | 57.6 |
| H | 4.33 | 4.2 |
| N | 7.53 | 7.3 |

EXAMPLE 3

5-(3,5-dicarboxy-phenylazo)-2-hydroxy-phenylacetic acid 12 g of 5-(3,5-bis-(methoxycarbonyl)-phenylazo)-2-hydroxyphenylacetic acid, 350 ml of water and 7 g of sodium hydroxide were boiled for 1 hour. 50 ml of ethanol was added, and the solution was diluted with water to 500 ml. The hot solution was acidified with hydrochloric acid to pH 2 and cooled. The crystals were filtered off, washed with water and dried.

Yield 12 g.
Melting point >260° C.
NMR analysis confirmed the identity of the substance.

| Elemental analysis: | | |
|---|---|---|
| | Calculated | Found |
| C | 55.82 | 55.6 |
| H | 3.51 | 3.4 |
| N | 8.14 | 7.9 |

EXAMPLE 4

5-(3,4-dicarboxy-phenylazo)-2-hydroxy-phenylacetec acid 6 g of 5-(3,4-bis-methoxycarbonyl)-phenylazo)-2-hydroxyphenylacetic acid and 3.9 g of sodium hydroxide dissolved in 100 ml of water were boiled for 45 minutes. The solution was acidified with hydrochloric acid and cooled, the crystals were filtered off and washed with water. They were dried for 4 hours at 100° C.

Yield: 5.3 g.
Melting point 208° C.

| Elemental analysis: | | |
|---|---|---|
| | Calculated | Found |
| C | 55.82 | 55.9 |
| H | 3.51 | 3.7 |
| N | 8.14 | 7.8 |

EXAMPLE 5

5-(3,4-bis-(ethoxycarbonyl)-phenylazo)-2-hydroxy-phenylacetic acid 27 g of diethyl-5-nitro-benzene-1,3-dicarboxylate was dissolved in 400 ml of acetic acid, and 1 g of 10% palladium on carbon, suspended in 10 ml of hydrochloric acid, was added. The suspension was hydrogenated, filtered and evaporated. The residue was leached with ethyl acetate and dried. The hydrochloride was suspended in 150 ml of water, 50 ml of tetrahydrofuran, 10 ml of hydrochloric acid, and was cooled with 50 g of ice. It was diazotized with 7 g of sodium nitrite dissolved in 30 ml of water. The diazonium salt solution was poured onto an ice-cooled solution of 30 g 2-hydroxy-phenylacetic acid and 24 g sodium hydroxide in 200 ml of water. The solution was acidified after 15 seconds with acetic acid and extracted with chloroform. The chloroformic phase was dried, treated with active carbon and evaporated. The evaporation residue was leached gently with chloroform, the residue then being dissolved in 300 ml of ethanol. 250 ml of hot water was added, and the solution was treated with active carbon. The solution was cooled to 30° C. and the product was filtered off and dried for 4 hours in vacuo at 100° C.

Yield 19 g.
Melting point 198° C. (melting point bench).
NMR analysis confirmed the structure of the substance.

| Elemental analysis: | | |
|---|---|---|
| | Calculated | Found |
| C | 59.99 | 60.1 |
| H | 5.03 | 5.1 |
| N | 7.00 | 6.6 |

EXAMPLE 6

The biological effect of compounds according to the present invention is illustrated by the following experiments:

The compound of Example 2 was studied in respect of its inhibitory effect on human PGDH isolated from placenta.

Radioactively labelled prostaglandin PGF 2 was incubated with the enzyme as according to Berry, C. N. et al., Biochem. Pharmacol. 1983, Vol. 32, p. 2863.

The compound of Example 2 was added in various concentrations, and the inhibition was measured as stated above.

The compound showed a 50% PGDH inhibition at a concentration of 28 nM. When similarly tested against PGDH from rat colon the compound gave 50% PGDH inhibition at 56 nM. For comparison, it may be mentioned that the known substances IV and V

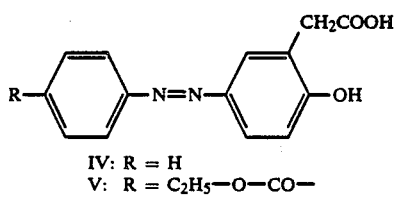

IV: R = H
V: R = C₂H₅—O—CO— produced 50% inhibition of human PGDH at concentrations of 12 000 nM (compound IV) and 290 nM (compound V) respectively. It should be noted that (V) is the strongest inhibitor of this type known in the literature.

No inhibition whatever of cyclooxygenase could be detected at concentrations of from 10 to 1,000 nM.

We claim:

1. An azo compound having the structure

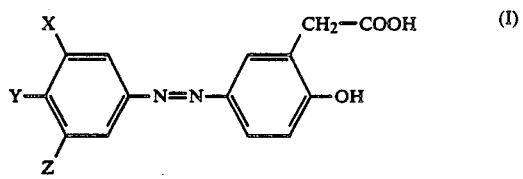

in which:
Y is hydrogen, and
X and Z are carboxy or lower alkoxycarbonyl,
or the lactones or salts of said azo compound.

2. An azo compound according to claim 1 in which X and Z are identical.

3. An azo compound according to claim 2 in which X and Z are lower alkoxycarbonyl.

4. An azo compound according to claim 3 in which X and Z are methoxycarbonyl or ethoxycarbonyl.

5. A pharmaceutical composition containing a therapeutical amount of a compound according to claim 1.

* * * * *